(12) United States Patent
Higham

(10) Patent No.: US 6,558,709 B2
(45) Date of Patent: May 6, 2003

(54) CALCIUM PHOSPHATE COMPOSITION AND METHOD OF PREPARING SAME

(75) Inventor: Paul Higham, Ringwood, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/754,882

(22) Filed: Jan. 5, 2001

(65) Prior Publication Data

US 2002/0127280 A1 Sep. 12, 2002

(51) Int. Cl.[7] .......................... A61K 33/42; A61K 9/14; A61K 47/00; C01B 25/00; C04B 12/02
(52) U.S. Cl. ...................... 424/602; 106/690; 106/691; 423/299; 423/304; 423/305; 423/306; 424/490; 424/493; 424/494; 424/495; 424/601; 424/606; 514/769; 514/772; 514/781; 514/951; 514/952
(58) Field of Search ................. 424/490, 493, 424/494, 495, 601, 602, 606; 514/769, 772, 781, 951, 952; 106/690, 691; 423/299, 304, 305, 306

(56) References Cited

U.S. PATENT DOCUMENTS

| | | | |
|---|---|---|---|
| 4,832,955 A | 5/1989 | Snipes et al. | 424/456 |
| 4,863,743 A | 9/1989 | Hsiao et al. | 424/476 |
| 4,880,610 A | 11/1989 | Constantz | 423/309 |
| RE33,161 E | 2/1990 | Brown et al. | 423/308 |
| RE33,221 E | 5/1990 | Brown et al. | 423/308 |
| 4,929,447 A | 5/1990 | Yang | 424/440 |
| 4,983,730 A | 1/1991 | Domeshek et al. | 536/69 |
| 5,047,031 A | 9/1991 | Constantz | 606/77 |
| 5,092,888 A | 3/1992 | Iwamoto et al. | 623/23.58 |
| 5,336,264 A | 8/1994 | Constantz et al. | 424/423 |
| 5,589,191 A | 12/1996 | Ukigaya et al. | 424/480 |
| 5,651,984 A | 7/1997 | Powell | 424/465 |
| 5,820,632 A | 10/1998 | Constantz et al. | 423/308 |
| 5,824,339 A | 10/1998 | Shimizu et al. | 424/466 |
| 5,976,507 A | 11/1999 | Wong et al. | 424/52 |
| 6,002,065 A | 12/1999 | Constantz et al. | 423/308 |

OTHER PUBLICATIONS

Composite of Calcium Phosphate Cement and Protein Bioadhesive Setting Reactions, Compressive and Diametral Tensile Strength, IADR 1991, Abstract No. 2410, R. Strausburg et al, pp. 1–10.

Effects of Additives on Setting Reaction of Calcium Phosphate Cement, AADR 1992, Abstract No. 666, N Sanin et al., pp. 1–10.

Skeletal Repair by in Situ Formation of the Mineral Phase of Bone, Constantz et al., Mar. 24, 1995, pp. 1796–1799.

Primary Examiner—Michael G. Hartley
Assistant Examiner—Frank Choi
(74) Attorney, Agent, or Firm—Lerner, David, Littenberg, Krumholz & Mentlik, LLP

(57) ABSTRACT

A method for controlling the formation of a hydroxyapatite bone filler from dry calcium phosphate precursors in an aqueous solution uses coated sodium phosphate powder. The sodium phosphate powder is coated with a water soluble cellulose. Until the cellulose dissolves in the aqueous solution setting of the calcium phosphate cements proceeds slowly but when the exposed sodium phosphate particles start to solubilize in the aqueous solution the setting rate increases.

24 Claims, No Drawings

CALCIUM PHOSPHATE COMPOSITION AND METHOD OF PREPARING SAME

BACKGROUND OF THE INVENTION

The field of this invention is in the preparation of calcium phosphate minerals for bone cement or bone filler applications. More specifically, this invention relates to a calcium phosphate bone cement which consists of a mixture of tetra-calcium phosphate and di-calcium phosphate in an aqueous mixture, which mixture then sets to form a bone cement with a substantial portion of the cement being hydroxyapatite.

Hydroxyapatite is the major natural building block of bone and teeth. It has been found useful in fixing fractures and bone defects to use bone cements which are formed by combining calcium and phosphate precursors in an aqueous solution which initially forms a paste but then hardens into a hydroxyapatite bone cement. Hydroxyapatite has a calcium to phosphorous ratio of approximately 1.67 which is generally the same as the calcium phosphate ratio in natural bone structures. The paste may be placed in situ prior to setting in situations where bone has been broken, destroyed, degraded, become too brittle or has been the subject of other deteriorating effects. Numerous calcium phosphate bone cements have been proposed such as those taught by Brown and Chow in U.S. Pat. Nos. Reissue 33,161 and 33,221 and by Constantz in U.S. Pat. Nos. 4,880,610 and 5,047,031, the teachings of these patents are incorporated herein by reference.

It has been well known since the initial use of calcium phosphate cements that the addition of sodium phosphate solutions, potassium phosphate solutions or sodium carbonate solutions to the aqueous setting solution of the calcium phosphate precursors can speed setting times. This is documented in the Chow et al. April, 1991 IADR Abstract No.: 2410 and AADR, 1992 Abstract No.: 666 and was well known to those skilled in the art prior to these publications. In addition, such is discussed in Constantz et al. U.S. Pat. Nos. 5,336,264, 5,820,632 and 6,002,605.

Controlling bone cement or filler setting time is important because it is necessary for the material to be initially flowable and then moldable but it also must be able to set in place even though quantities of blood may be present. This blood creates problems in providing too much fluid so that the mineral salts are either washed away or dissolved prior to setting up. Obviously, if the material sets up too quickly, the surgeon has difficulty in mixing the calcium phosphate mineral cement and then placing it at the necessary bone site.

It has been found that the addition of sodium phosphate to the aqueous solutions mixed with the dry calcium phosphate precursors speeds the setting of calcium phosphate bone cement, such as those disclosed by Brown and Chow. However, the sodium phosphate may cause the setting to occur more quickly than desired. Thus, a method for better controlling the setting time of such cements has been found desirable.

SUMMARY OF THE INVENTION

It is an object of the invention to provide a method for better controlling the setting times of calcium phosphate cements.

It is an additional object of the invention to provide a method for coating dry highly water soluble sodium phosphate particles with a water soluble material, the thickness of which can be varied to control the time in which the sodium phosphate particle solubilize in the aqueous setting solution. The dry coated sodium phosphate particles are pre-mixed with the dry powdered calcium phosphate precursors to thereby better control setting times.

These objects are achieved by a method for forming a calcium phosphate bone treatment material comprising mixing at least one dry calcium phosphate mineral power in an aqueous solution causing a reaction which forms a settable material. The rate of reaction is controlled by mixing, as a dry ingredient, a water soluble alkaline/acidic material, such as $Na_2HPO_4$ or a water soluble $NaH_2PO_4$ which materials have a water soluble coating, with the dry calcium phosphate mineral precursors prior to or simultaneously with the addition of the aqueous solution. The rate of reaction may be controlled by varying the thickness of the water soluble coating surrounding the water soluble alkaline/acidic material and may be controlled to a lesser degree by the concentration of the sodium phosphate in the mixture. The water soluble coating may be cellulose, such as cellulose acetate, cellulose acetate butyrate, hydroxypropyl cellulose, hydroxymethyl cellulose, carboxymethyl cellulose, hydroxyethyl cellulose, sodium ethyl cellulose sulfate, sodium carboxymethyl cellulose and combinations thereof. The alkaline/acidic material may be any material which is water soluble and forms a solution containing the phosphate ion.

The calcium phosphate mineral may be tetra-calcium phosphate, di-calcium phosphate, tri-calcium phosphate, mono-calcium phosphate and mono-calcium phosphate monohydrate, hydroxyapatite, either alone or in combinations.

DETAILED DESCRIPTION

In the preferred embodiment the calcium phosphate dry component is composed of tetra-calcium phosphate and di-calcium phosphate in a 1:1 molar ratio to which about 1% by weight of a powdered and coated sodium phosphate mineral has been added. The preferred sodium phosphate is either $Na_2HPO_4$ or $NaH_2PO_4$ which is coated with a cellulose coating by using the method described herein. The amount of sodium phosphate dry particles added, by weight, can be varied to vary the setting time. In the preferred embodiment, from 0.5% to 1.5% by weight of the coated sodium phosphate dry mineral powder is added to the dry calcium phosphate precursors. To ensure complete solubility of the sodium phosphate particles in the aqueous wetting solution, the initial size of the sodium phosphate powder to be coated should be less than 100 $\mu$ in size with the coated particles being no more than 100 $\mu$ microns in size.

The amount of coated sodium phosphate, by weight, in the powdered component must be varied depending on the liquid to powder ratio used in the bone cement. For example, if the liquid to powder ratio of aqueous solution to calcium phosphate coated sodium phosphate (by weight) is 0.25 and approximately 10 grams total of calcium phosphate/coated sodium phosphate dried powder are used (i.e. the 10 grams including 0.75% by weight coated sodium phosphate powder), then if the liquid to powder ratio is raised to 0.3 (i.e. 20% above the 0.25 ratio) then the sodium phosphate, by weight, must be increased 20% in order to maintain the same setting time (i.e. to 0.9%).

Furthermore, setting times can be varied by varying the thickness of the coating of the sodium phosphate particles. Having a somewhat thicker coating results in a somewhat longer time for the coating to dissolve thereby releasing the phosphate ions. The increase in coating thickness can be accomplished by increasing the amount of cellulose acetate butyrate in the solution or allowing the solution to sit for a longer period of time (30 to 60 minutes rather than 15 to 30 minutes) after the sodium phosphate particles are added.

Example 1 details the process for coating the sodium phosphate particles with the results of the calcium phosphate cement setting times for the coated and uncoated particles listed in Table 1.

EXAMPLE 1

Into a round bottom flask were added 150 ml of ethyl acetate and 2.0 g of cellulose acetate butyrate particles (CAB, MW=200,000, butyrate content=17%, from Acros/Fisher) stirring continuously. A water bath was placed under the flask for cooling it to below room temperature (25° C.). The dry ingredients were allowed to dissolve for 2–3 hours to form a homogenous solution. Then 1.0 g of sodium phosphate particles less than 100 μ in size were added and suspended in the solution for about 15–30 minutes, continuing the stirring. Then 150–200 ml of n-Hexane was added dropwise at the rate of 80–100 drops per minute for 5–10 minutes continuing the stirring. After the addition of the n-Hexane, ice water was added to the bath to help harden the formed microcapsules. After 5–10 minutes, cold (below room temperature) n-Hexane was added to wash loose particles off the microcapsules. The microcapsules are recovered by decantation, washed with cold n-Hexane and air or vacuum dried.

The process of Example 1 was done for both $NaH_2PO_4$ and $Na_2HPO_4$ particles (Na-Phos) less than 100 μ in size. The effect of coated vs. uncoated phosphate powders on setting time of a tetra-calcium phosphate plus di-calcium phosphate cement as taught in U.S. Pat. No. Reissue 33,161 are shown below in Table 1:

TABLE 1

| Liquid/Powder Ratio* | Set Time (Coated Na-Phos Powder) | Set Time (Uncoated Na-Phos Powder) |
|---|---|---|
| For $NaH_2PO_4$ powder: | | |
| 0.25 | 40 min. | 12 min. |
| 0.30 | >60 min. | 22 min. |
| Liquid/Powder Ratio* | Set Time (Coated Powder) | Set Time (Uncoated Powder) |
| For $Na_2HPO_4$ powder: | | |
| 0.25 | 39 min. | 18 min. |
| 0.30 | >70 min. | 26 min. |

*Liquid/"total powder" ratio with the "total powder" consisting of tetra-calcium phosphate, di-calcium phosphate and 0.75% sodium phosphate powder by weight.

As can be seen from Table 1, setting times were dramatically increased by using the sodium phosphate particles coated by the method of the present invention with cellulose acetate butyrate versus uncoated particles. As is well known in the prior art whether the sodium phosphate particles are included in the cement as dried particles or previously solubilized in the aqueous component, it is the concentration of the sodium and phosphate ions in solution which determines the setting times. The use of a coating delays the release of the sodium and phosphate ions thereby retarding the setting time by allowing a slow setting initial phase followed by a faster setting phase (after the coating dissolves and the sodium phosphate solubilizes). This method of controlling setting time is superior to varying the concentration of uncoated sodium phosphate which works to a limited extent but as the concentration of phosphate ions in solution decreases, the affect on setting time becomes erratic and less robust. With the present invention, the concentration of phosphate ions can be kept constant by mixing coated sodium phosphate particles having coatings of varying thicknesses or mixing coated and uncoated particles in the dry calcium phosphate cement precursors.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for forming a calcium phosphate bone treatment material comprising:
    reacting at least one calcium phosphate mineral as a dry ingredient with an aqueous solution causing a reaction which forms a settable material; and
    controlling the rate of the reaction by dissolving a water soluble phosphate compound having a water soluble coating as a dry ingredient in the calcium phosphate mineral and aqueous solution and varying the amount of coated phosphate compound as the aqueous solution to dry ingredient ratio varies wherein the particle size of the coated phosphate compound is no more than 100 microns.

2. The method as set forth in claim 1 where the reaction is controlled by varying the thickness of the coating surrounding the water soluble phosphate compound.

3. The method as set forth in claim 2 wherein the water soluble coating is cellulose.

4. The method as set forth in claim 3 having a coating selected from the group consisting of cellulose acetate, cellulose acetate butyrate, hydroxypropyl cellulose, hydroxymethyl cellulose, carboxymethylethyl cellulose, hydroxyethyl cellulose, sodium ethyl cellulose sulfate, sodium carboxymethyl cellulose and a combination thereof.

5. The method as set forth in claim 1 wherein the coated phosphate compound is selected from the group consisting of potassium phosphates, sodium phosphates and a combination thereof.

6. The method as set forth in claim 5 wherein the at least one calcium phosphate mineral includes tetra-calcium phosphate.

7. The method as set forth in claim 1 wherein the calcium phosphate mineral includes at least one member selected from the group of tetra-calcium phosphate, di-calcium phosphate, tri-calcium phosphate, mono-calcium phosphate monohydrate, hydroxyapatite and a combination thereof.

8. The method as set forth in claim 1 wherein the coated water soluble phosphate compound makes up 0.5 to 1.5% of the combined weight of the dry ingredients.

9. A method for forming a settable calcium phosphate cement comprising:
    providing a dry powder comprising at least one calcium phosphate mineral and at least one water soluble phosphate compound encapsulated within a water soluble coating in a first container; and
    mixing the dry calcium phosphate mineral and the encapsulated phosphate compound with an aqueous solution contained in a second container which dissolves the encapsulated phosphate compound and forms a basic solution which controls a setting time of the calcium phosphate cement and wherein the amount of encapsulated phosphate compound is varied depending on the ratio of dry powder to aqueous solution to produce a setting time or maintain a desire setting time wherein the particle size of the encapsulated phosphate compound is no more than 100 microns.

10. The method as set forth in claim 9 where the reaction is controlled by varying the thickness of the coating surrounding the encapsulated phosphate compound.

11. The method as set forth in claim 9 wherein the water soluble coating of the encapsulated phosphate compound is cellulose.

12. The method as set forth in claim 11 having a coating selected from the group consisting of cellulose acetate, cellulose acetate butyrate, hydroxypropyl cellulose, hydroxymethyl cellulose, carboxymethylethyl cellulose, hydroxyethyl cellulose, sodium ethyl cellulose sulfate, sodium carboxymethyl cellulose and a combination thereof.

13. The method as set forth in claim 9 wherein the encapsulated phosphate compound is selected from the group consisting of potassium phosphates, sodium phosphates and a combination thereof.

14. The method as set forth in claim 13 wherein the at least one calcium phosphate mineral includes tetra-calcium phosphate.

15. The method as set forth in claim 9 wherein the calcium phosphate mineral includes a member selected from the group of tetra-calcium phosphate, di-calcium phosphate, tri-calcium phosphate, mono-calcium phosphate monohydrate, hydroxyapatite and a combination thereof.

16. The method as set forth in claim 9 wherein the encapsulated water soluble phosphate compound makes up 0.5 to 1.5% of the combined weight of the dry ingredients.

17. A kit for forming a settable calcium phosphate cement comprising:

a dry ingredient comprising at least one calcium phosphate mineral and a water soluble phosphate compound encapsulated within a water soluble coating in a first container; and an aqueous solution in a second container, the amount of encapsulated phosphate compound varying as the ratio of dry powder to aqueous solution to produce a setting time or to maintain a desired setting time wherein the particle size of the encapsulated phosphate compound is no more than 100 microns.

18. The kit as set forth in claim 17 where the reaction is controlled by varying the thickness of the encapsulation of the phosphate compound.

19. The kit as set forth in claim 17 wherein the water soluble coating is cellulose.

20. The kit as set forth in claim 17 having a coating selected from the group consisting of cellulose acetate, cellulose acetate butyrate, hydroxypropyl cellulose, hydroxymethyl cellulose, carboxymethylethyl cellulose, hydroxyethyl cellulose, sodium ethyl cellulose sulfate, sodium carboxymethyl cellulose and a combination thereof.

21. The kit as set forth in claim 17 wherein the encapsulated phosphate compound is selected from the group consisting of potassium phosphates, sodium phosphates and a combination thereof.

22. The kit as set forth in claim 21 wherein the at least one calcium phosphate mineral includes tetra-calcium phosphate.

23. The kit as set forth in claim 17 wherein the calcium phosphate mineral includes a member selected from the group of tetra-calcium phosphate, di-calcium phosphate, tri-calcium phosphate, mono-calcium phosphate monohydrate, hydroxyapatite and a combination thereof.

24. The kit as set forth in claim 17 wherein the water soluble encapsulated phosphate compound make up 0.5 to 1.5% of the combined weight of the dry ingredients.

* * * * *